United States Patent [19]

Oliver et al.

[11] 4,166,461
[45] Sep. 4, 1979

[54] SURGICAL DRAPE

[75] Inventors: Don W. Oliver; John L. Dale, both of Memphis, Tenn.

[73] Assignee: The Buckeye Cellulose Corporation, Cincinnati, Ohio

[21] Appl. No.: 876,827

[22] Filed: Feb. 10, 1978

[51] Int. Cl.² ............................................. A61F 13/00
[52] U.S. Cl. ................................................. 128/132 D
[58] Field of Search ..................... 128/132 D, 292, 163

[56] References Cited

U.S. PATENT DOCUMENTS

| | | | |
|---|---|---|---|
| 3,343,534 | 9/1967 | Keoughan et al. | 128/132 D |
| 3,742,944 | 7/1973 | Sease | 128/132 D |
| 3,777,749 | 12/1973 | Collins | 128/132 D |
| 3,881,476 | 5/1975 | Bolker et al. | 128/132 D |
| 3,911,912 | 10/1975 | Krebs et al. | 128/132 D |
| 3,955,569 | 5/1976 | Krzewinski et al. | 128/132 D |
| 3,998,221 | 12/1976 | Collins | 128/132 D |

*Primary Examiner*—Lawrence W. Trapp
*Attorney, Agent, or Firm*—Timothy N. Trop; John V. Gorman; Richard C. Witte

[57] ABSTRACT

A surgical head drape of a single sheet of flexible material which is a barrier to bacterial migration provided with a pair of opposed and spaced apart side slits extending oppositely inwardly of both side edges to define a connecting tab portion integrally connecting a base sheet panel portion adapted to be inserted under the patient's head and covering the head end portion of an operating table with a turban sheet panel portion adapted to be wrapped around the patient's head with the turban sheet panel portion folded to overlie the base sheet panel portion during initial presentation (i.e., approach to the patient). The slits are dog-legged or jogged at the inner end portion thereof defining an offset connecting fold line therebetween and the drape is folded therearound to position the turban sheet panel portion on the base sheet panel portion with the leading edges of the base and turban sheet panel portions being offset so that the base sheet panel portion extends beyond the turban sheet panel portion. The drape is further folded to encourage aseptic handling during presentation and enabling it to be picked up and applied or positioned to drape the patient's head and the underlying head end portion of the operating table without the nurse having to reposition her hands on the drape so that she may therefore maintain complete control of the drape and thereby substantially reduce the danger of contamination.

14 Claims, 12 Drawing Figures

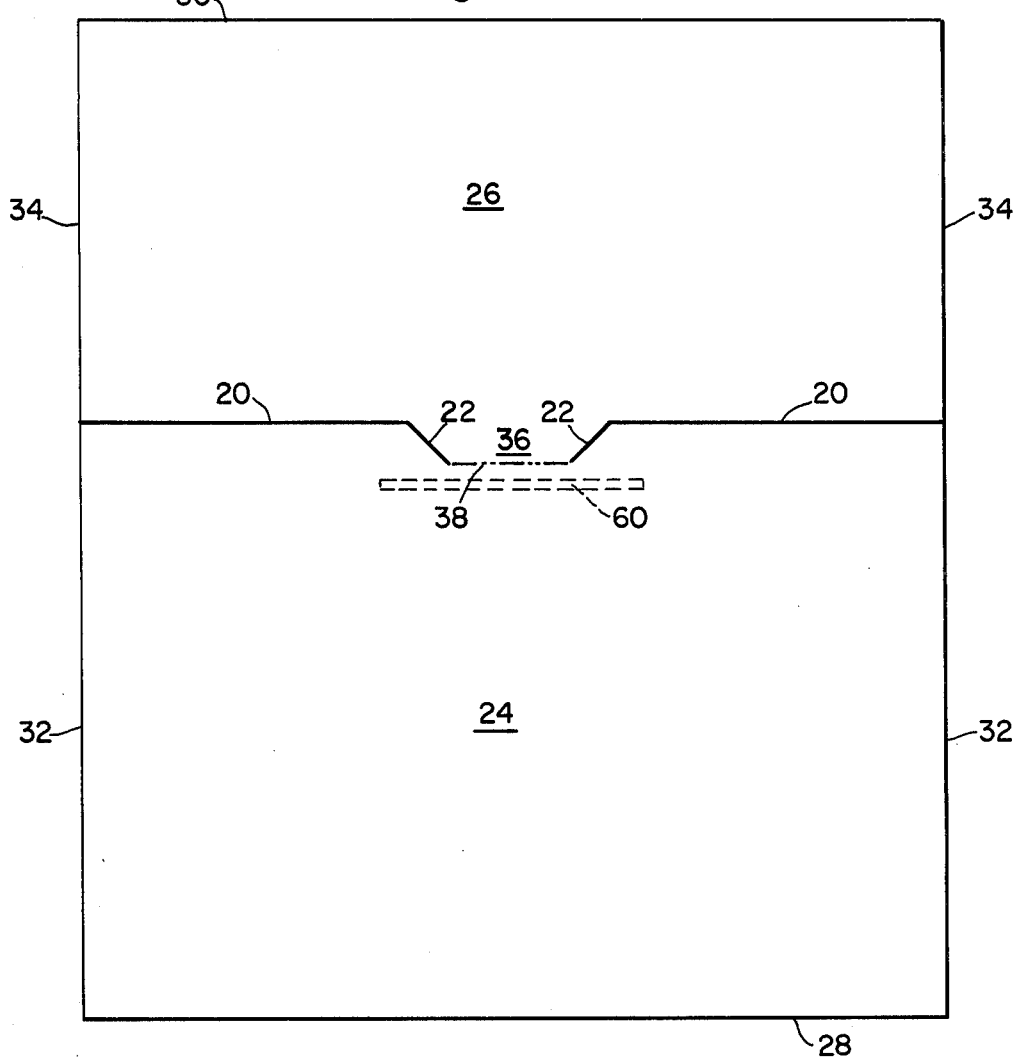
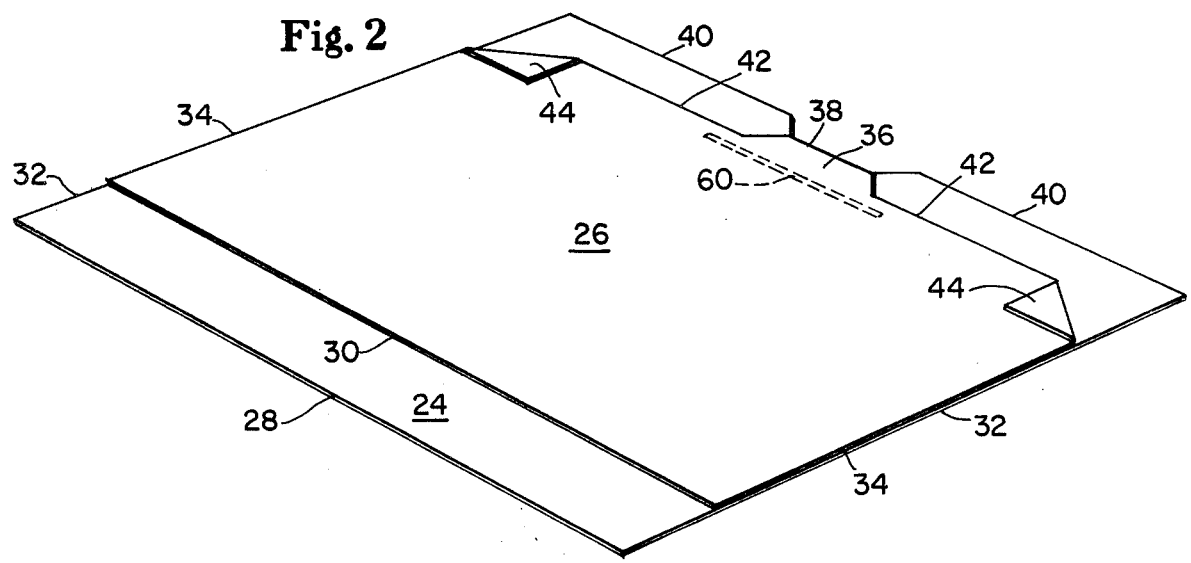

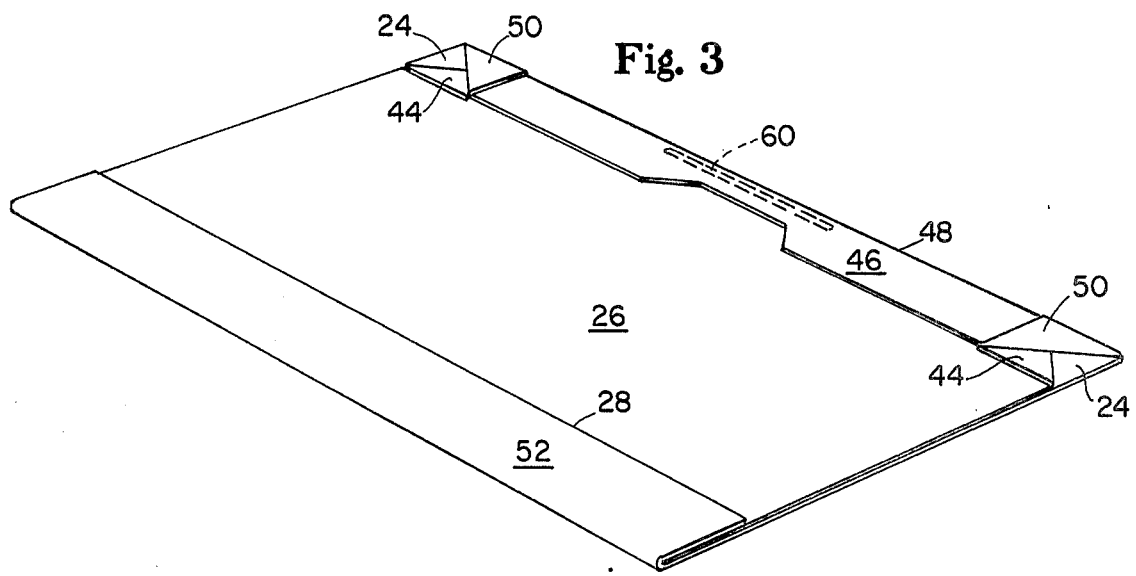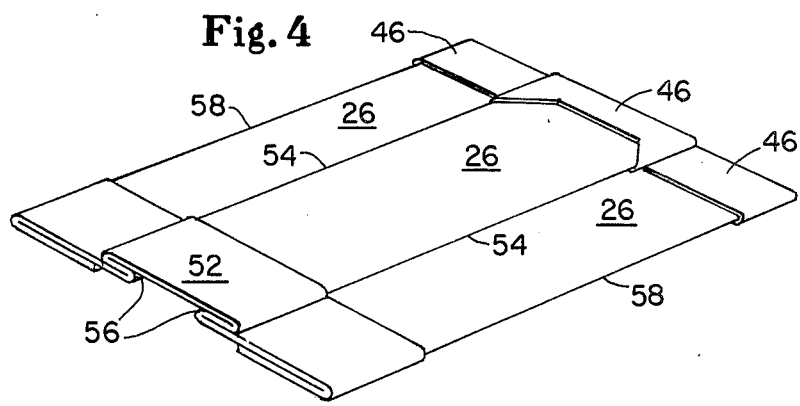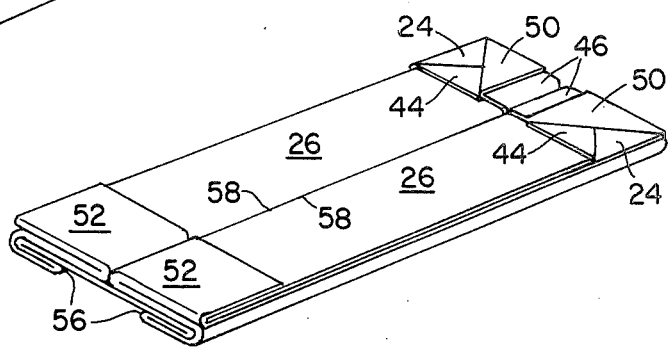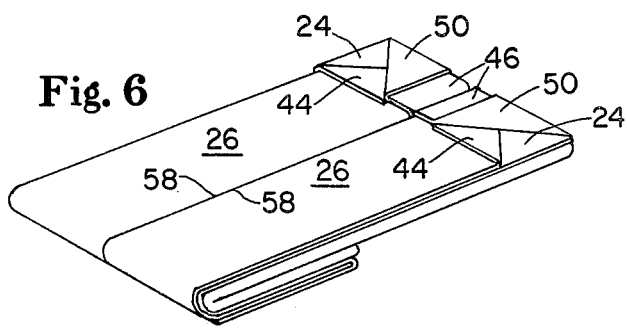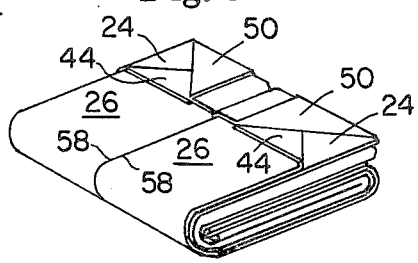

SURGICAL DRAPE

FIELD OF THE INVENTION

This invention pertains to drapes which are used to cover the operative area and/or portions of the patient's anatomy during surgical procedures. The drape of the present invention finds particular utility in surgical procedures involving the head, such as eye surgery, dental surgery, nose surgery, facial surgery, throat surgery, ear surgery and the like by enabling a nurse to simply and easily drape the head end of the operating table and provide a full turban wrap to isolate the patient's head and hair. The present invention finds especial utility in connection with such drapes that are manufactured from nonwoven materials and intended for single use only.

DESCRIPTION OF THE PRIOR ART

When surgery involving the head is undertaken, conventional draping procedures utilizing standard multiple utility drape items often involve a rather complicated draping process.

One method, for example, for draping a patient's head involves the use of two operating room towels and towel clips and requires the placing of two towels superposed one above the other in more or less centered position, beneath the patient's head. The ends of the upper towel are then brought upwardly around the sides of the head to a position overlying the forehead and are then secured together, in turban-like fashion, as with the aid of one or more towel clamps. The lower towel remains in position between the patient's head and the operating room table.

This draping technique is disadvantageous in several respects. First of all, the risk of contamination during the draping process is greater than is generally desired. The flat uniform sized towels are hard for the nurse to aseptically handle while avoiding contact of her hands with either the patient's head and hair or the operating table, either of which will contaminate the nurse's hands. Secondly, since ends of the towel are joined together in the forehead region with towel clips, the latter frequently are in the way when the surgery is subsequently performed. Furthermore, this procedure is quite time-consuming, often requiring a minute or more of time which may be very critical, both in terms of the welfare of the patient and operating room resources. In addition these steps can be distracting to the operating room team and provide multiple opportunities for contamination of the operative site.

With the advent of single-use or disposable surgical drape items, the design and tailoring of specialized drape items, folded and pre-packaged in sterile packages has become increasingly practicable and feasible. Hence, a number of specialty head drape designs have recently become available.

For example, Krzewinski and Gorrie U.S. Pat. No. 3,955,569 dated May 11, 1976 describes a surgical drape which has a main sheet with a cuff at the top end thereof secured to the upper surface of the main sheet to provide a hand receiving pocket in the drape. A strip of adhesive is secured to the lower surface of the main sheet near the top edge of the drape. The pocket in the drape receives the hands of a nurse who may easily and quickly secure the drape to the desired part of the patient's body by bringing the adhesive into contact with the patient and running her fingers back and forth over the adhesive strip lying under the pocket. This drape design avoids some of the disadvantages of using two towels, but does not provide for a full turban wrap of the patient's head and hair as is preferred by some surgeons.

Krebs and Arps U.S. Pat. No. 3,911,912 dated Oct. 14, 1975, by way of further example, describes a specialty surgical head drape design wherein there is provided a main sheet having a folded cuff along one edge for receiving the nurse's hands and, attached thereto, a second drape adapted to be wrapped around a body member such as a patient's head. This design also reduces the risk of contamination and does provide a full turban wrap, but still requires the assembly of two separate drape elements. Moreover, a carefully thought-out and executed folding and unfolding arrangement is highly desirable for specialty surgical drapes to maximize the convenience to the surgical team as well as to minimize risks of contamination and the Krebs et al patent is substantially silent in this connection.

Surgical draping (Manual on Control of Infection in Surgical Patients, American College of Surgeons, J. B. Lippincott Company, 1976, page 85) "is important as a means of demarcating, maintaining, and protecting a limited area prepared for the operation by cleansing and degerming techniques." As used herein, the phrase "a barrier to bacterial migration" is intended to encompass broadly any material capable of providing such means of demarcating, maintaining and protecting, and is not intended to be limited, for example, to absolute impermeability under any or all circumstances. Hence, dry, sterilized, conventional linen drapes are generally continued to be recognized as acceptable draping materials. Single use or disposable surgical drapes are generally inherently or treated to be at least liquid repellant.

OBJECTS OF THE INVENTION

Accordingly, it is a primary object of the present invention to provide a surgical head drape that will reduce the time consumed in draping, the risk of contamination of the operative site, and distraction of the operating room team.

Another primary object of the present invention, in addition to the foregoing object is to provide a unitized surgical head drape which is yet made from a single sheet of flexible sheet-like material which is a barrier to bacterial migration and which enables provision of a full turban wrap of a patient's head and hair.

Another primary object of the present invention, in addition to each of the foregoing objects, is to provide a novel and improved surgical specialty drape, which is disposable after a single use, and which is especially adapted for surgical procedures requiring draping of a patient's head, such as for throat, eye, nose, facial or oral surgery.

Yet another primary object of the present invention, in addition to each of the foregoing objects, is to provide novel and improved folding of a surgical head drape which enables it to be picked up and applied or positioned to drape the patient's head and the underlying head end portion of the operating table without the nurse having to reposition her hands on the drape so that she may therefore maintain complete control of the drape and thereby substantially reduce the danger of contamination.

The invention resides in the combination, construction, arrangement, disposition, design and folding of the various component parts and elements incorporated in an improved surgical drape in accordance with the principles of this invention. The present invention will be better understood and objects and important features other than those specifically enumerated above will become apparent when consideration is given to the following details and description, which when taken in conjunction with the annexed drawing describes, discloses, illustrates and shows a preferred embodiment or modification of the present invention and what is presently considered and believed to be the best mode of practicing the principles thereof. Other embodiments or modifications may be suggested to those having the benefit of the teachings herein, and such other embodiments or modifications are intended to be reserved especially as they fall within the scope and spirit of the subjoined claims.

SUMMARY OF THE INVENTION

A surgical head drape of a single sheet of flexible material which is a barrier to bacterial migration provided with a pair of opposed and spaced apart side slits extending oppositely inwardly of both side edges to define a connecting tab portion integrally connecting a base sheet panel portion adapted to be inserted under the patient's head and covering the head end portion of an operating table with a turban sheet panel portion adapted to be wrapped around the patient's head with the turban sheet panel portion folded to overlie the base sheet panel portion during initial presentation (i.e., approach to the patient). The slits are dog-legged or jogged at the inner end portion thereof defining an offset connecting fold line therebetween and the drape is folded therearound to position the turban sheet panel portion on the base sheet panel portion with the leading edges of the base and turban sheet panel portion being offset so that the base sheet panel portion extends beyond the turban sheet panel portion. The drape is further folded to encourage aseptic handling during presentation and enabling it to be picked up and applied or positioned to drape the patient's head and the underlying head end portion of the operating table without the nurse having to reposition her hands on the drape so that she may therefore maintain complete control of the drape and thereby substantially reduce the danger of contamination. To achieve this, the leading and trailing edges of the base sheet panel portion are cuff folded over the turban sheet panel portion and the superposed cuff folds, turban sheet panel portion and base sheet panel portion are together fan folded laterally inwardly to form a pair of tuck folds under the central portion of the drape and a pair of parallel zig-zag folds disposing a pair of folds stacked adjacent one another above the tuck folds. The adjacent leading and trailing corners of the forwardmost cuff and adjacent turban sheet panel portions are oppositely triangularly folded to provide a pair of superposed generally opposed triangular pick-up folds, enabling the nurse to insert her index fingers between the pick-up folds and the leading corners of the turban sheet to grasp them between thumbs and index fingers during presentation to control the sequence of unfolding. The trailing end portion of the drape is roll folded forwardly under the pick-up folds and leading end portion to a final package fold, then packaged and sterilized.

BRIEF DESCRIPTION OF THE DRAWINGS

FIG. 1 is a plan view of a drape in accordance with the present invention in an unfolded condition;

FIG. 2 illustrates a similar drape folded to form a pair of superposed sheet portions with the corners of the upper or turban sheet portion proximal the fold line further folded back to form a first set of triangular pick up folds;

FIG. 3 illustrates a similar drape further folded to form a cuff along the leading edge with the corners thereof further folded back to form a second set of triangular pick up folds and with the trailing edge portion of the lower or base sheet folded upwardly over the turban sheet trailing edge;

FIGS. 4–7, inclusive, illustrate similar drapes sequentially further folded to a final package configuration for sterilization and storage;

DESCRIPTION OF A PREFERRED EMBODIMENT

Figure 8:
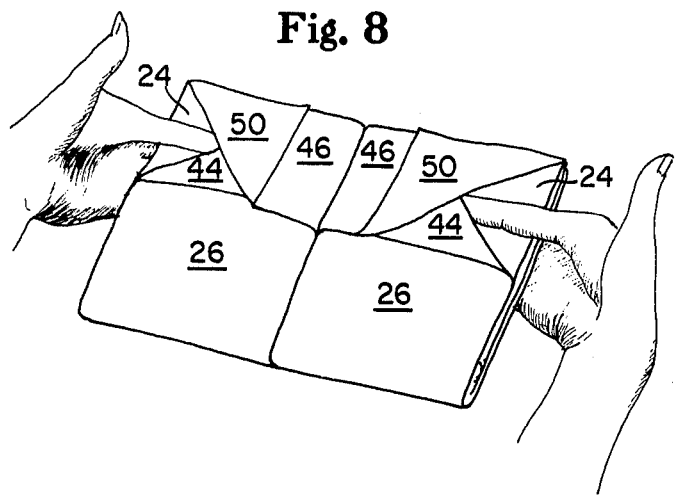
FIGS. 8–11, inclusive, illustrate similar drapes in the sequence of being unfolded for use.

With reference now to the drawing, there is shown and illustrated an improved head drape constructed and folded in accordance with the present invention which is fabricated of a generally rectangular sheet of flexible sheet material which is a barrier to bacterial migration. As will be appreciated by those skilled in the art, surgical drapes may be fabricated of many diverse materials which form a barrier to bacterial migration. Hence, the head drape of the present invention may be made of substantially any woven, nonwoven, or plastic material. Preferably, however, the drape comprises a flexible, drapable nonwoven fabric laminate and, more preferably, the nonwoven fabric laminate is liquid repellent to prevent strike-through of liquids, such as water, blood, and the like, which are normally encountered during surgery. Most preferably, the head drape of the present invention is fabricated of a fluid repellent laminate comprising a continuous filament nonwoven centerply latex bonded to a pair of facing tissue paper plies as more completely described and disclosed in co-pending patent application Ser. No. 741,640 filed Nov. 15, 1976 by Larry L. LaFitte and James B. Camden and assigned to the Buckeye Cellulose Company. The full and complete disclosure of this co-pending application Ser. No. 741,640 is hereby incorporated herein by reference, as fully and completely as if fully set forth hereat.

With particular reference now to FIG. 1 it may be seen that the improved head drape of the present invention may be of generally rectangular configuration having, for example, a width of approximately 44" and a length of approximately 50". The drape is provided with a pair of slits 20 directed generally oppositely inwardly from each of the side edges at a distance of, for example, about 17" terminating at dog-legged or jogged slit extensions 22 extending therefrom at approximately a 45° angle so as to divide the drape into a base sheet panel portion 24 and a turban sheet panel portion 26 defined between the slits 20–22 and the respective end edges 28 and 30, respectively, of the drape. The base sheet panel portion 24 and the turban sheet panel portion 26 are further defined by their respective side edges 32 and 34. Further, the region between the jogged or dog-leg slit portions 22 defines a connecting tab portion 36. The slits 20 may be spaced approximately 20" from the edge 30 of the turban sheet 26 and the connecting tab portion 36 may have a depth of about 2".

The drape may be folded for use by initially folding the turban sheet panel portion 26 over the base sheet 24 along an offset connecting fold line 38 between the ends of the jogged slit portions 22, i.e., whereat the connecting tab portion 36 joins the base sheet panel portion 24 so that the turban sheet panel portion 26 is intermediate the longitudinal extent of the base sheet panel portion 24 and superpositioned thereon as illustrated in FIG. 2. In this configuration, with the end of the drape adjacent the continuous tab connector portion 36 considered the leading end, the edges of the slits 20 now define base sheet leading edges 40 and, spaced therefrom, approximately 4" in a trailing direction, turban sheet leading edges 42. The edges 28 and 30 may now be considered to define trailing edges to the base sheet panel portion 24 and turban sheet panel portion 26, respectively. First triangular pickup folds 44 may now be formed on the leading corners of the turban sheet panel portion 26 for a purpose which will become apparent hereinafter.

Next, a leading cuff 46 is formed by upwardly folding the base sheet leading end and continuous tab connector portion 36 upwardly over the leading edges 42 of the turban sheet panel portion 26 thereby defining a leading edge fold 48 at the leading edge of the drape. Second triangular pick-up folds 50 may now be formed on the cuff 46 trailing corners oppositely directed from the first triangular pick-up folds 44 adjacent and overlapping the first pick-up folds 44, all as shown in FIG. 3. The trailing portion of the base sheet 24 extending beyond the turban sheet 26 may now be upwardly folded around the trailing edge 30 of the turban sheet 26 to define a trailing cuff 52.

Next, and with reference now to FIG. 4, the drape may be tuck folded inwardly along spaced apart fold lines 54 and 56 on either side of the longitudinal centerline passing through the continuous tab connector portion 36 and under the center portion of the drape. The side edges may be further cuffed under along fold lines 58 to define a pair of parallel zig-zag folds which may then be further cuffed upwardly along the fold lines 54 to bring the side folds 58 stacked adjacent one another above the tuck folds and extending centrally up the drape, thereby positioning the overlapping triangular pick-up folds 44 and 50 on top, as shown in FIG. 5. Finally, the trailing end of the longitudinally folded drape may be roll folded forwardly under the leading end as shown in FIGS. 6 and 7 to a package fold. The final package fold configuration for sterilization and storage is illustrated in FIG. 7.

Figure 9:
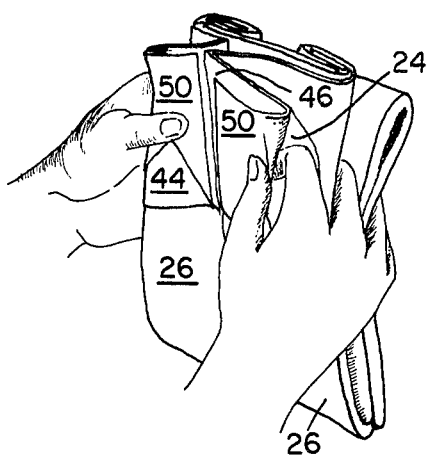
Figure 11:
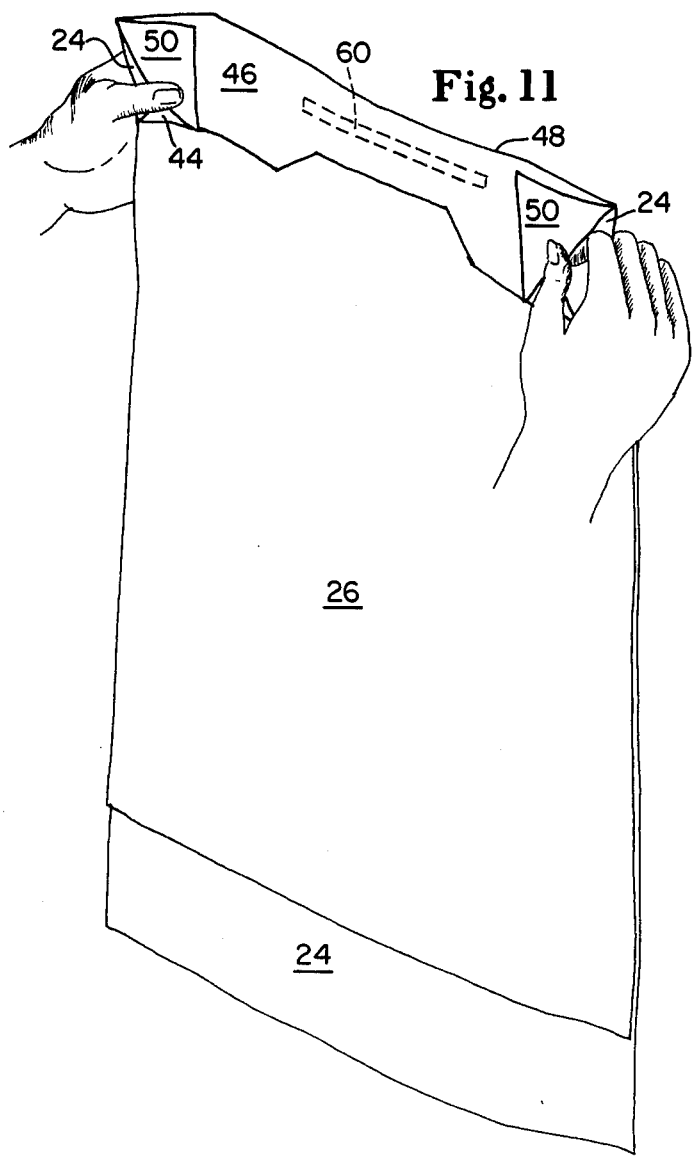
Figure 10:
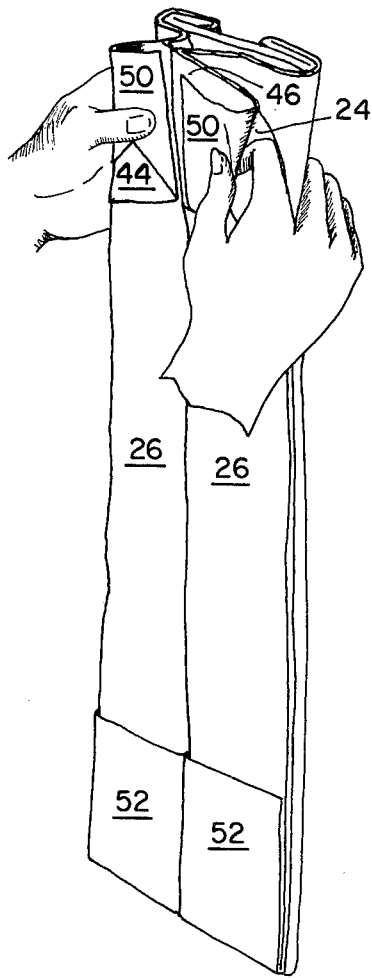

The package folded drape as shown in FIG. 7, if properly picked up, may be aseptically unfolded and applied or positioned to drape the patient's head and the underlying end portion of the operating table without the nurse having to reposition her hands. She may, therefore, maintain complete control of the drape and thereby substantially reduce the likelihood of contamination. In order to provide for such advantageous control of the drape, it is merely necessary that the nurse insert her index fingers beneath the triangular pick-up folds 44 and 50 and grasp the triangular pick-up folds between her index fingers and thumbs, as shown in FIG. 8. Simultaneously, the second finger of each hand should be inserted between the roll folded trailing end portion of the drape and the leading end portion of the drape and the third and fourth fingers disposed beneath the roll folded trailing end portion. The roll folded trailing end may therefore be grasped between the second and third fingers while the leading end portion is grasped between the index and second fingers, as shown in FIG. 9. When so grasped, the package folded drape may be picked up and carried to the patient. When the pressures between the second and third fingers are relaxed, the trailing end portion of the drape will unroll while the trailing cuff 52 retains control of the turban sheet panel portion 26, as shown in FIG. 10.

Figure 12:
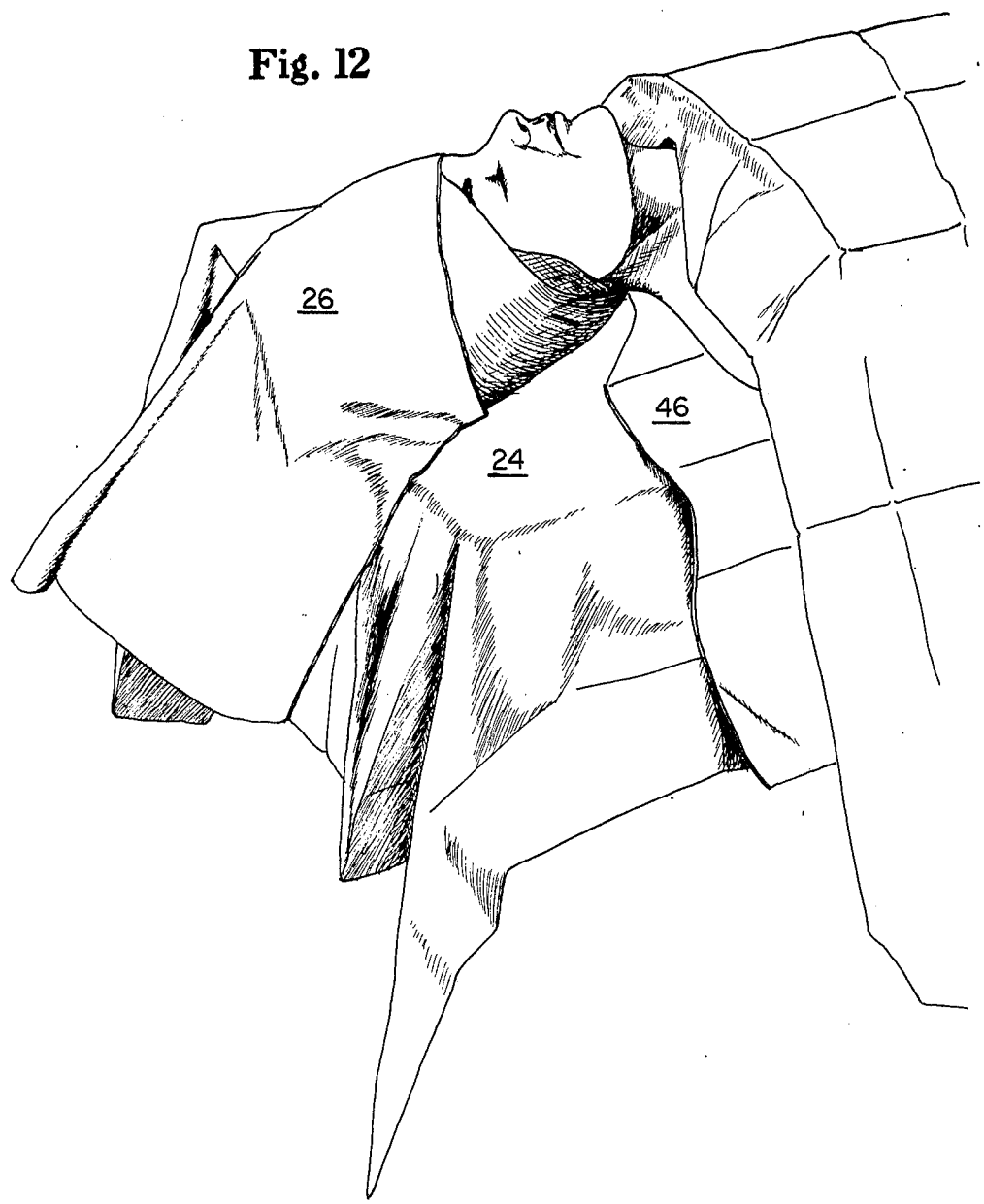
FIG. 12 illustrates a similar drape as used to drape a patient for surgery.

Next, the nurse has merely to release the pressures between her index and second fingers and spread her hands apart to further open the drape while maintaining her grasp of the leading end portion of the drape between her index fingers and thumbs. The leading end portion of the drape may now be slid under the patient's head, thereby draping the base sheet under the patient's head and over the end of the operating table while preventing the turban sheet panel portion 26 from contacting the operating table or the base sheet panel portion 26 from contacting the patient's head or hair. Now merely sliding her thumbs down so as to release the triangular pick-up folds 50 while maintaining her grasp of the turban sheet leading end triangular pick-up folds 44 enables the nurse to wrap the turban sheet around the patient's head to complete the draping procedure as shown in FIG. 12. The turban sheet may then be taped, clamped, or the like, if desired.

The drape may also be provided with a strip of adhesive 60 on the bottom surface of the base sheet panel portion 24 adjacent the forward or leading edge fold 48. The length and width of the adhesive strip may be varied but, preferably, the adhesive strip is of sufficient length as to substantially be able to reach from ear to ear across a patient's forehead. The adhesive 60 may be protected prior to use with a releasably adhered protective covering. Any of the adhesives well known in the art may be used, the only requirements being that the adhesive be non-toxic, stable to ordinary sterilization procedures, and removably adhereable to the body surface to which it will be applied. The adhesive 60 enables the drape to be alternatively utilized, not as a turban wrap drape, but to be draped over the patient's head and adhered thereto as is preferred for some procedures.

While the invention has been described, disclosed, illustrated and shown in terms of an embodiment or modification which it has assumed in practice, the scope of the invention should not be deemed to be limited by the precise embodiments or modifications herein described, disclosed, illustrated or shown, such other embodiments or modifications being intended to be reserved especially as they fall within the scope and breadth of the claims here appended.

What is claimed is:

1. A unitized surgical head drape comprising a single generally rectangular sheet of flexible sheet material which is a barrier to bacterial migration provided with a pair of opposed and spaced apart side slits extending oppositely inwardly of both side edges to define a connecting tab portion integrally connecting a base sheet panel portion adapted to be disposed beneath a patient's head and covering the head end portion of an operating table with a turban sheet panel portion adapted to be turban wrapped around the patient's head.

2. Drape defined in claim 1 wherein said side slits are jogged at the inner end portion thereof defining an offset connecting fold line therebetween, said drape being folded therearound to position said turban sheet panel portion on said base sheet panel portion with the leading edges of said base and turban sheet portions defined by said slits being offset with the base sheet panel portion extending beyond said turban sheet portion.

3. Drape defined in claim 2 wherein said extending portion of said base sheet panel portion is cuff folded over said turban sheet panel portion.

4. Drape defined in claim 3 wherein the leading corners of said turban sheet panel portion and the trailing corners of said cuff fold are folded to provide a first and a second pair of overlapping triangular pickup folds for guiding a user's fingers between said folds and the subjacent base sheet panel portion.

5. Drape defined in claim 4 wherein the trailing end of said base sheet panel portion extends beyond the trailing edge of said turban sheet panel portion and is cuff folded therearound and the drape is further folded by a pair of tuck folds generally perpendicular said connecting fold line and spaced apart on either side thereof and a pair of parallel zig-zag folds disposing the side folds stacked adjacent one another above said tuck folds with said triangular pickup folds exposed on the upper surface of the drape.

6. Drape defined in claim 5 further roll folded under said triangular pick up folds to a package fold whereby a nurse can pick up the package, unfold it and apply it to a patient without repositioning her hands by inserting her index fingers between said triangular pick up folds and the underlying portion of said base sheet and grasping said triangular pick up folds between her index fingers and her thumbs, inserting her second fingers between said tuck folds and said roll folds and grasping said roll folds between her second and third fingers.

7. Drape defined in claim 6 fabricated of a nonwoven fabric for disposable one-time use.

8. A unitized surgical head drape comprising a generally rectangular base sheet panel portion adapted to be disposed beneath a patient's head and covering the head end portion of an operating table, and a generally rectangular turban sheet panel portion adapted to be turban wrapped around the patient's head, said base and turban sheet portions being fabricated of flexible sheet material which is a barrier to bacterial migration, said turban sheet panel portion being positioned on said base sheet panel portion with the leading edges of said base and turban sheet portions being offset with the base sheet panel portion extending beyond said turban sheet portion and said extending portion of said base sheet panel portion cuff folded over said turban sheet panel portion, the leading corners of said turban sheet panel portion and the trailing corners of said cuff fold being folded to provide a first and a second pair of overlapping triangular pickup folds for guiding a user's fingers between said folds and the subjacent base sheet panel portion.

9. Drape defined in claim 8 wherein the trailing end of said base sheet panel portion extends beyond the trailing edge of said turban sheet panel portion and is cuff folded therearound and the drape is further folded by a pair of tuck folds generally perpendicular the leading edge and spaced apart on either side of the center thereof and a pair of parallel zig-zag folds disposing the side edge portions stacked adjacent one another above said tuck folds with said triangular pickup folds exposed on the upper surface of the drape.

10. Drape defined in claim 9 further roll folded under said triangular pick up folds to a package fold whereby a nurse can pick up the package, unfold it and apply it to a patient without repositioning her hands by inserting her index fingers between said triangular pick up folds and the underlying portion of said base sheet and grasping said triangular pick up folds between her index fingers and her thumbs, inserting her second fingers between said tuck folds and said roll folds and grasping said roll folds between her second and third fingers.

11. Drape defined in claim 10 fabricated of a nonwoven fabric for disposable one-time use.

12. Method of folding a unitized surgical head drape having a generally rectangular base sheet panel portion adapted to be disposed beneath a patient's head and covering the head end portion of an operating table, and a generally rectangular turban sheet panel portion adapted to be turban wrapped around the patient's head, wherein said turban sheet panel portion is positioned on said base sheet panel portion with the leading edges of said base and turban sheet portions being offset with the base sheet panel portion extending beyond said turban sheet portion comprising, at least the steps of folding the extending portion of the base sheet panel portion over the turban sheet panel portion to form a cuff therearound, and folding the leading corners of said turban sheet panel portion and the trailing corners of said cuff fold to provide a first and a second pair of overlapping triangular pickup folds for guiding a user's fingers between said folds and the subjacent base sheet panel portion.

13. Method defined in claim 12 wherein the trailing end of said base sheet panel portion extends beyond the trailing edge of said turban sheet panel portion further comprising cuff folding the trailing edge portion of the base sheet panel portion over the trailing edge portion of the turban sheet panel and further folding a pair of tuck folds generally perpendicular the leading and trailing edges and spaced apart on either side of the center thereof and a pair of parallel zig-zag folds disposing the side edge portions stacked adjacent one another above such tuck folds with the triangular pick-up folds exposed on the upper surface of the drape.

14. Method defined in claim 13 further comprising roll folding under the triangular pick-up folds to a package fold whereby a nurse can pick up the package, unfold it and apply it to a patient without repositioning her hands by inserting her index fingers between the triangular pick up folds and the underlying portion of the base sheet and grasping the triangular pick-up folds between her index fingers and her thumbs, inserting her second fingers between the tuck folds and the roll folds and grasping the roll folds between her second and third fingers.

* * * * *